United States Patent [19]
Langevin et al.

[11] Patent Number: 6,055,048
[45] Date of Patent: Apr. 25, 2000

[54] OPTICAL-TO-TACTILE TRANSLATOR

[75] Inventors: Maurice L. Langevin, Indian Head, Md.; Philip I Moynihan, La Canada, Calif.

[73] Assignee: The United States of America as represented by the United States National Aeronautics and Space Administration, Washington, D.C.

[21] Appl. No.: 09/137,865

[22] Filed: Aug. 7, 1998

[51] Int. Cl.[7] .................................................. G01N 21/00
[52] U.S. Cl. ........................................ 356/237.1; 356/376
[58] Field of Search ................................ 356/237.1, 376

[56] References Cited

U.S. PATENT DOCUMENTS

| | | | |
|---|---|---|---|
| 4,972,501 | 11/1990 | Horyu | 382/53 |
| 5,803,740 | 9/1998 | Gesink et al. | 434/112 |

*Primary Examiner*—Frank G. Font
*Assistant Examiner*—Reginald A. Ratliff
*Attorney, Agent, or Firm*—John H. Kusmiss

[57] ABSTRACT

An optical-to-tactile translator provides an aid for the visually impaired by translating a near-field scene to a tactile signal corresponding to said near-field scene. An optical sensor using a plurality of active pixel sensors (APS) converts the optical image within the near-field scene to a digital signal. The digital signal is then processed by a microprocessor and a simple shape signal is generated based on the digital signal. The shape signal is then communicated to a tactile transmitter where the shape signal is converted into a tactile signal using a series of contacts. The shape signal may be an outline of the significant shapes determined in the near-field scene, or the shape signal may comprise a simple symbolic representation of common items encountered repeatedly. The user is thus made aware of the unseen near-field scene, including potential obstacles and dangers, through a series of tactile contacts. In a preferred embodiment, a range determining device such as those commonly found on auto-focusing cameras is included to limit the distance that the optical sensor interprets the near-field scene.

34 Claims, 3 Drawing Sheets

OPTICAL-TO-TACTILE TRANSLATOR

ORIGIN OF THE INVENTION

The invention described herein was made in the performance of work under a NASA contract, and is subject to the provisions of Public Law 96-517 (35 U.S.C. § 202) in which the Contractor has elected not to retain title.

TECHNICAL FIELD

The present invention relates generally to aids for the sight impaired, and more particularly to an optical translator for imaging a near-field scene and providing a tactile signal corresponding to said scene to enable the user to interpret obstacles and surroundings through touch which cannot be seen.

BACKGROUND ART

The blind and the sight impaired experience enhanced challenges in their day-to-day tribulations of every day life. One continuous challenge is that of navigating unfamiliar territory. The inability to fully comprehend near-field surroundings poses a threat to the safety of the sight impaired and can limit the sight impaired's ability to travel freely. To assist the sight impaired, the traditional ambulatory aid is the cane. The cane provides a two- to three-meter zone in front of the individual where large objects can be perceived through contact. The cane is a simple approach, and doubtless has been around since man has walked the Earth.

The cane is not the perfect solution, however. A cane is typically moved along the ground's surface as the individual walks, and thus can fail to detect obstacles which are not on the ground, such as those at head level. A cane cannot detect anything until the user maneuvers it in contact with an obstacle, which poses a problem since the user typically cannot see the obstacle, and thus the obstacle can evade detection. A cane provides no feedback as to the size or shape of the obstacle, or whether the obstacle is moving or dangerous. Relying on a cane, the individual must walk in a narrowly defined path behind the cane in order to remain as safe from peril as possible. In sum, while a cane is better than nothing, the absence of any meaningful feedback and the inherent dangers of moving in unfamiliar territory without a full near field comprehension make walking with a cane a dangerous proposition.

In some instances the cane has been replaced by the guide dog, an animal trained to lead the visually impaired. A guide dog is an expensive alternative, and has many of the drawbacks as the cane and includes a few additional drawbacks. Like the cane, a guide dog typically provides no feedback with respect to the obstacles in proximity to the user. A guide dog has a slightly broader range than the cane, but relegates the user to a passive stance rather than an active posture in determining obstacles. A guide dog is subject to illness and injury, and decision making is left to an animal, albeit a presumably well trained animal. Thus, there are inherent limitations and drawbacks associated with the use of a guide dog as well.

STATEMENT OF THE INVENTION

The shortcomings of the prior art have been overcome by the present invention, in which an optical sensor translates a near-field image to a digital signal. A processor receives the digital signal and converts the digital signal to a command which is received by an apparatus providing a physical signal the user, preferably in the form a series of pin-type contacts which can deliver a tactile interpretation of the near-field image. The present invention preferably includes an active pixel sensor focal-plane array for converting the near-field image to a digital signal and a range finder for limiting the optical field to approximately 5 meters. The focal-plane array of active pixel sensor (APS) processes the near-field image and generates electrical signals which correspond to the near-field images.

The processor receives the signal and performs various refinements such as edge enhancement, gray-scale development, and clutter rejection based on preset algorithms, and develops an outline of the near-field scene. The outline is transmitted to a tactile transmitter such as a grid of pins or a contact point which supports movement in an X and Y direction. The tactile transmitter communicates the outline to the user by either reproducing the outline on the user's skin or produces a pattern which is recognized by the user similar to a Braille system. The system is small enough to be worn comfortably on a sensitive part of the body such as the forehead or hand to facilitate transmission of the tactile signal.

BRIEF DESCRIPTION OF THE DRAWINGS

The exact nature of this invention, as well as its objects and advantages, will become readily apparent upon reference to the following detailed description when considered in conjunction with the accompanying drawings, in which like reference numerals designate like parts throughout the figures thereof, and wherein:

FIG. 4b is an example of a set of pin positions on the tactile transmitter corresponding to the near field image of FIG. 4a.

DETAILED DESCRIPTION OF THE INVENTION

The following description is provided to enable any person skilled in the art to make and use the invention and sets forth the best modes contemplated by the inventors of carrying out their invention. Various modifications, however, will remain readily apparent to those skilled in the art, since the general principles of the present invention have been defined herein specifically to provide an optical-to-tactile translator system for communicating optical fields to tactile signals.

Figure 1:
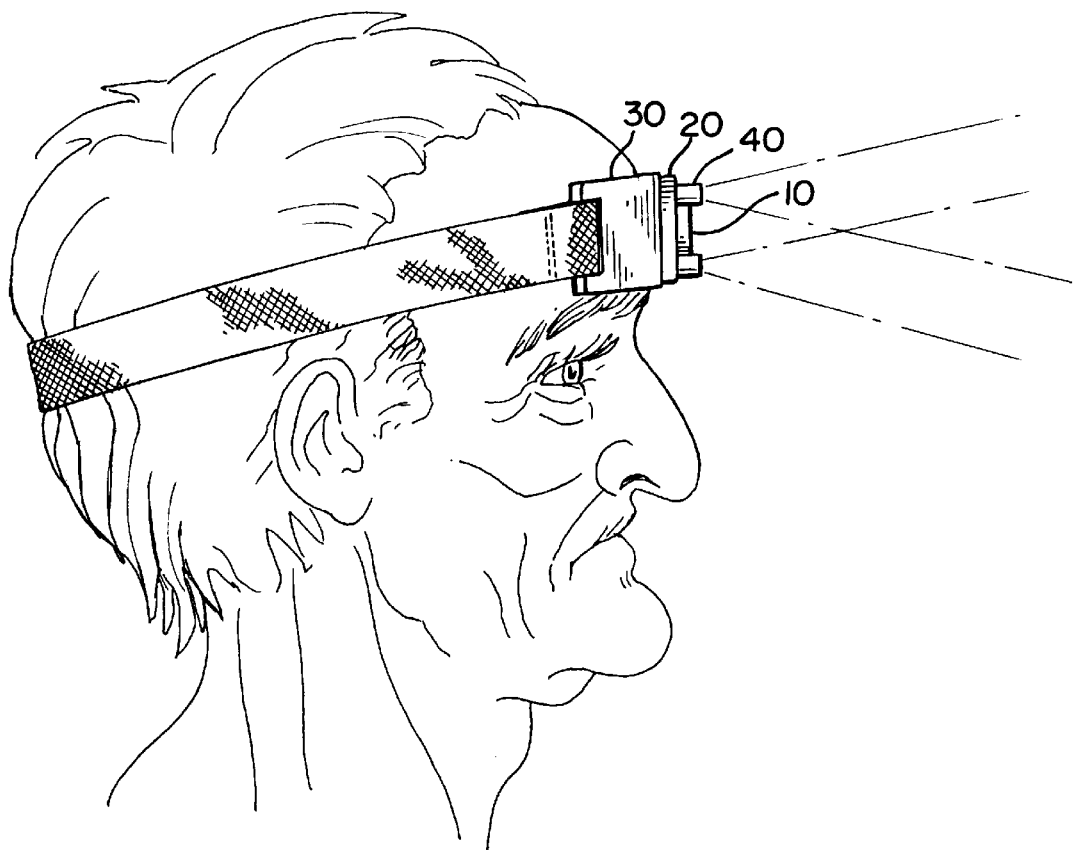
FIG. 1 is a side view of one preferred embodiment of the system disposed on the forehead of a user.
Figure 2:
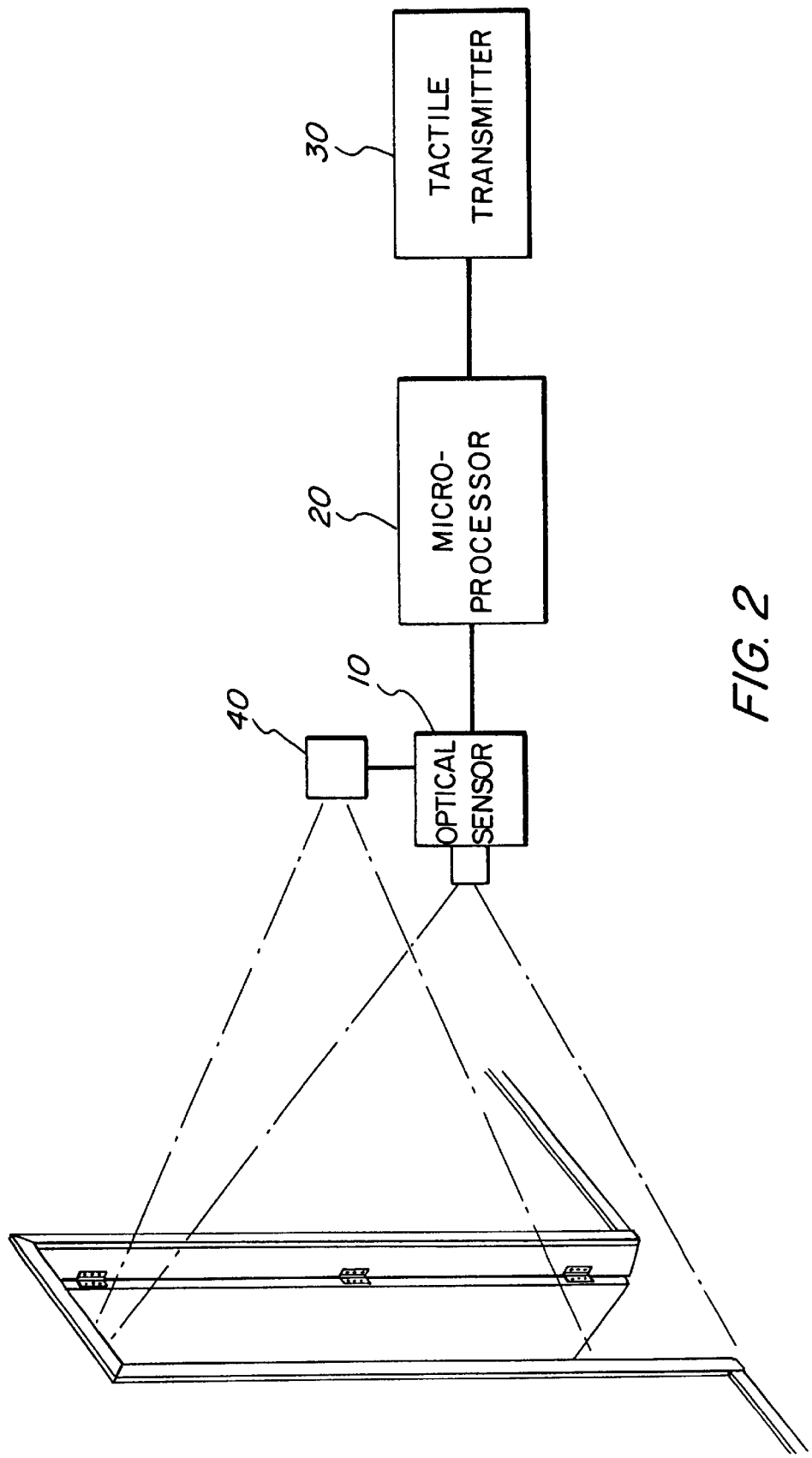
FIG. 2 is a schematic diagram of the system.

FIGS. 1 and 2 disclose a preferred embodiment of the present invention, which comprises an optical sensor 10, and microprocessor 20, and a tactile transmitter 30 for delivering a tactile signal to the user. FIG. 1 shows the optical sensor 10, the microprocessor 20, and the tactile transmitter 30 in a housing member mounted on the user's forehead by a headband. In the preferred embodiment, the system will include a range-determining device 40 such as those commonly found on automatic cameras for limiting the range of the interpreted optical field to those images within approximately 5 meters of the user. This range is arbitrarily chosen to approximate a three-pace buffer for a user to avoid an obstacle in his or her path. The distance is, of course, a matter of preference and the scope of the invention does not depend on the range of the system. However, the range-determining device 40 will reduce the amount of processing the user must interpret, which in turn will make using the system simpler and easier to learn.

The range-determining device 40 cooperates with the optical sensor 10, which is preferably a detector comprised of an array of active pixel sensors such as that developed by the Jet Propulsion Laboratory in Pasadena, Calif. The function of the optical sensor is to obtain a near-field scene and generate therefrom a visual interpretation in the form of a signal which can be easily transmitted, such as a digital signal. Active pixel sensors (APS) technology utilizes active transistors within each pixel of the detector array to buffer the photo-signal. This technology enables superior edge-detection resolution, as individual pixels are not affected by neighboring pixels and so no "bleed-over" occurs. The result is a sharper image from a relatively small component than is found in conventional optical detectors. APS sensors require only a single low-power supply and are small enough (in some cases, less than one (1) square inch of visible, planar area) to be used for the present application without the need of further miniatuization.

The optical sensor using APS technology operates in the far ultraviolet, visible, and near infrared (up to 1 micron wavelength) spectrum of silicon response bands, uses a single five (5) volt dc power supply, and features an area array of very small pixels (less than twenty micron pitch). It is produced with the same commercially available complementary metal-oxide-semiconductor (CMOS) device fabrication process used in nearly all modern microprocessors, memory, and logic chips. This allows on-chip integration of detector array elements, on-pixel amplifiers, and on-chip electronic analog-to-digital conversion and timing and control circuits.

The system uses a microprocessor 20 to convert the output from the optical sensor 10 to a useful format. The output from the microprocessor 20 is a shape signal corresponding to the image received by the optical sensor 10. Algorithms can be included to recognize common shapes such as, for example, traffic lights, trees, cars, doorways, and so forth. Such algorithms are used in military applications to recognize and evaluate predetermined targets, and have been found to be quite effective. Similar algorithms can be employed by the present invention to recognize common obstacles and structures. Moreover, similar to sighted persons' response to international non-verbal signs, a set of simple pre-selected symbolic representations can be developed for common obstacles such as stairs, curbs, doors, traffic lights, etc. which would provide an efficient means for conveying information. For example, a set of ascending stairs could be symbolized as two 'L's turned on their axis (faced down) and staggered to the right. Descending stairs could use the same symbol but staggered to the left instead. Alternately, the image received from the APS sensor can be converted to a simple outline of the predominant or largest shape discernable in the near-field scene.

The microprocessor can also be used to convey additional information. A voice chip can be employed to emit aural signals or cues, which may be especially helpful in the initial stages of learning the system. The voice chips can be used in combination with said tactile transmitter to alert and instruct users regarding conditions important to them, and well as information regarding the status of the system such as low batteries or malfunction. As for the scene interpreted from the optical sensor, depth and movement can be interpreted using gray scales and translated using intensity of contact, for example. Another alternative is the interpretation of basic colors, which can be achieved using the APS optical sensors and standard LCD-color-isolation processes. Color in the tactile signal can be conveyed using low frequency vibrations, for example. In this manner, traffic lights can be interpreted as red or green.

Figure 3:
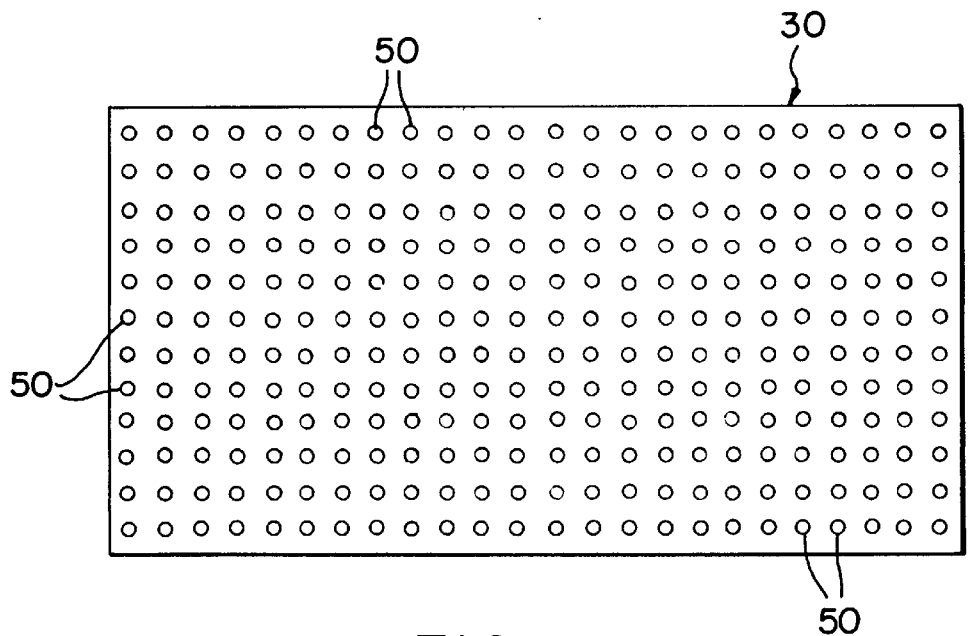
FIG. 3 is a plan view of one preferred embodiment of a tactile transmitter.

A tactile transmitter 30 is connected to the microprocessor 20 and receives the shape signal corresponding to the near-field scene. The tactile transmitter 30 implements a tactile pattern on the user corresponding to the designated shape signal. The tactile transmitter 30 is desirably a rectangular patch of, for example, two inches by three inches in length. To translate the shape signal received by the microprocessor 20 to a tactile signal on the user, a grid or array of pin-like members 50 (see FIG. 3) is operably disposed over the user's designated contact area. Commands from the microprocessor cause the pin-ike members 50 to move, thereby contacting the user at the designated surface. A series of contacts by different pin-like members will produce a signal which corresponds to a shape, and said shape can be recognized by the user. Alternately, instead of an array of pins, a single pin which is movable in an X and Y direction, i.e., parallel to the surface of the user, as well as the Z direction (in and out of the plane of the surface of the user) may be used to trace out a shape.

While a single patch is illustrated, it is conceivable that a plurality of patches strategically located at separate locations on the user and operating in conjunction with one another, may well provide a spatial logic which is not translated as well by a single patch. Thus, the present invention may operate with a plurality of patches 30. The microprocessor 20 operates the pins 50 to move according to the shape signal to touch the user in such a manner that the shape is conveyed to the user via contact with the pins 50. The sequence of near-field scene being (a) converted to a digital signal, which is (b) translated to a shape signal, which is (c) converted to a tactile signal, can occur at multiple times per second depending upon the limits of the recognition of the user. In a preferred embodiment, the number of cycles will be adjustable so that as the user gradually learns the system, additional cycles can be implemented to provide more information. It is presumed that a learning will occur with this invention which will allow the user to interpret the tactile signals with greater ease as the device is used.

Figure 4A:
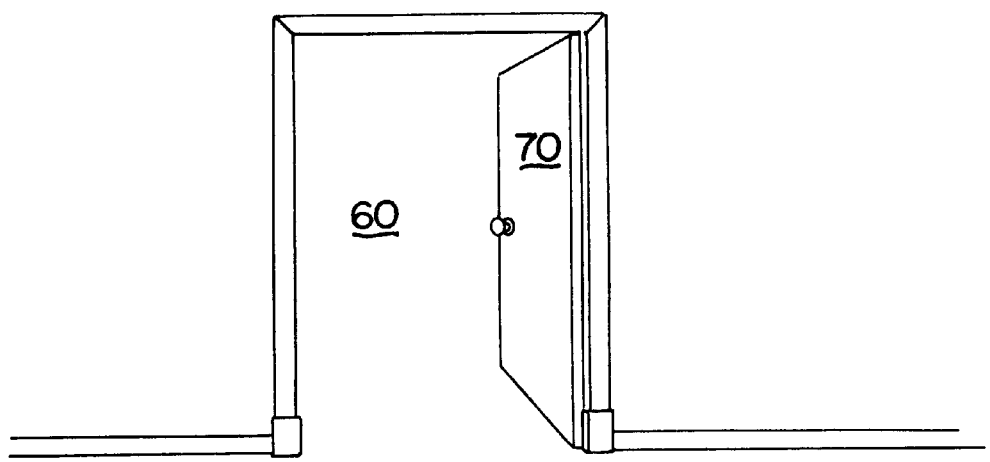
FIG. 4a is an example of a near field optical image.
Figure 4B:
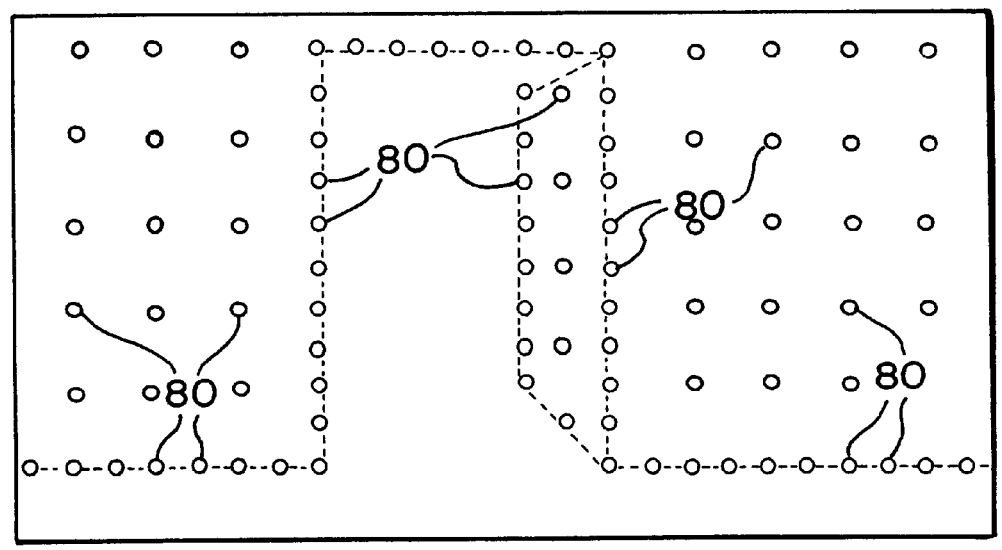

As an example of the function of the present invention, FIG. 4a illustrates a possible near-field image of a doorway 60 and a door 70 that may be encountered by a visually impaired person. The image of a doorway 60 and a partially open door 70 would ordinarily require a visually impaired person to engage in a trial and error approach to navigate the doorway. In the present invention, when the image 60,70 is within the range of the range-determining device 40, the optical sensor 10 interprets the optical field and generates a digital signal corresponding to the image 60,70. The microprocessor 20 receives the digital signal from the optical sensor and generates a shape signal based on included algorithms. In this example, an outline 80 is created based on the image 60,70, and the outline 80 is communicated to the tactile transmitter 30 with instructions to generate the outline 80 using the grid of pins 50. From this instruction, the tactile transmitter 30 produces the pattern of pins corresponding to the outline 80 which may be interpreted by the user as a doorway 60 and partially open door 70 (See FIG. 4b).

Those skilled in the art will appreciate that various adaptations and modifications of the just-described preferred embodiment can be configured without departing from the scope and spirit of the invention. For example, the method and apparatus by which the tactile signal is delivered to the user can be achieved in various ways, such as a single moving pin similar to a plotting device rather than a grid of pins. The optical sensor 10, while preferably employing APS technology due to size and resolution advantages, may alternatively use a more conventional optical sensor technology. Similarly, while a range determining device 40 is preferably included to reduce the amount of processing necessary, the operation of the present invention does not rely on the range determining device 40 and if desired, can be excluded. Thus, it is to be understood that, within the scope of the appended claims, the invention may be practiced other than as specifically described herein.

What is claimed is:

1. An optical-to-tactile translator for interpreting a near-field scene and communicating a tactile signal to a user based on said near-field scene comprising:

an optical sensor to obtain said near-field scene and generate a visual interpretation signal corresponding to said near-field scene;

a tactile transmitter adapted to transmit a tactile shape signal to the user; and a microprocessor in communication with said optical sensor for receiving said visual interpretation signal from said optical sensor, and based on said received visual interpretation signal, performing gray-scale development and edge enhancement on said received visual interpretation signal, generating said tactile shape corresponding to said edge enhanced visual interpretation signal, communicating said tactile shape signal to said tactile transmitter, and further commanding said tactile transmitter to transmit the tactile shape signal to the user.

2. An optical-to-tactile translator for interpreting a near-field scene and communicating a tactile signal to a user based on said near-field scene comprising:

an optical sensor to obtain said near-field scene and generate a visual interpretation signal corresponding to said near-field scene;

a range-determining device cooperating with said optical sensor to limit the distance that the optical sensor obtains the near-field scene;

a tactile transmitter adapted to transmit a tactile shape signal to the user;

a microprocessor in communication with said optical sensor for receiving said visual interpretation signal from said optical sensor, and based on said received visual interpretation signal, generating said tactile shape corresponding to said received visual interpretation signal, communicating said tactile shape signal to said tactile transmitter, and further commanding said tactile transmitter to transmit the tactile shape signal to the user.

3. The optical-to-tactile translator of claim 2 wherein the distance that the optical sensor obtains the near-field image is five meters.

4. The optical-to-tactile translator of claim 1 wherein the optical sensor is less than one square inch.

5. The optical-to-tactile translator of claim 1 wherein the optical sensor comprises a plurality of active pixel sensors (APS).

6. The optical-to-tactile translator of claim 5 wherein the optical sensor is less than one square inch.

7. The optical-to-tactile translator of claim 1 wherein the optical sensor operates in the ultraviolet, visible, and infrared spectrum.

8. The optical-to-tactile translator of claim 1 wherein the optical sensor operates on a maximum of a 5 volt power supply.

9. The optical-to-tactile translator of claim 1 wherein the visual interpretation signal generated by the optical sensor comprises a digital signal.

10. An optical-to-tactile translator for interpreting a near-field scene and communicating a tactile signal to a user based on said near-field scene comprising:

an optical sensor to obtain said near-field scene and generate a visual interpretation signal corresponding to said near-field scene;

a tactile transmitter adapted to transmit a tactile shape signal to the user;

a microprocessor in communication with said optical sensor for receiving said visual interpretation signal from said optical sensor, and based on said received visual interpretation signal, generating said tactile shape corresponding to said received visual interpretation signal, communicating said tactile shape signal to said tactile transmitter, and further commanding said tactile transmitter to transmit the tactile shape signal to the user; and wherein said microprocessor further comprises a recognition algorithm for recognizing common obstacles and, if an obstacle is recognized by said recognition algorithm, generating a pre-selected symbol shape signal corresponding to said recognized common obstacle.

11. An optical-to-tactile translator for interpreting a near-field scene and communicating a tactile signal to a user based on said near-field scene comprising:

an optical sensor to obtain said near-field scene and generate a visual interpretation signal corresponding to said near-field scene;

a tactile transmitter adapted to transmit a tactile shape signal to the user;

a microprocessor in communication with said optical sensor for receiving said visual interpretation signal from said optical sensor, and based on said received visual interpretation signal, determining an outline of said near-filed scene, generating said tactile shape corresponding to the outline of said near-field scene, communicating said tactile shape signal to said tactile transmitter, and further commanding said tactile transmitter to transmit the tactile shape signal to the user.

12. An optical-to-tactile translator for interpreting a near-field scene and communicating a tactile signal to a user based on said near-field scene comprising:

an optical sensor to obtain said near-field scene and generate a visual interpretation signal corresponding to said near-field scene;

a tactile transmitter adapted to transmit a tactile shape signal to the user;

a microprocessor in communication with said optical sensor for receiving said visual interpretation signal from said optical sensor, and based on said received visual interpretation signal, generating said tactile shape corresponding to said received visual interpretation signal, communicating said tactile shape signal to said tactile transmitter, and further commanding said tactile transmitter to transmit the tactile shape signal to the user; and a voice chip operated by said microprocessor for delivering signals to said user in addition to said tactile shape signals.

13. The optical-to-tactile translator of claim 12 wherein said voice chip further delivers aural signals corresponding to a status of said optical-to-tactile translator.

14. An optical-to-tactile translator for interpreting a near-field scene and communicating a tactile signal to a user based on said near-field scene comprising:
- an optical sensor to obtain said near-field scene and generate a visual interpretation signal corresponding to said near-field scene;
- tactile transmitter adapted to transmit a tactile shape signal to the user;
- a microprocessor in communication with said optical sensor for receiving said visual interpretation signal from said optical sensor, and based on said received visual interpretation signal, generating said tactile shape corresponding to said received visual interpretation signal, communicating said tactile shape signal to said tactile transmitter, and further commanding said tactile transmitter to transmit the tactile shape signal to the user; and
- wherein an intensity of the tactile shape to the user is varied to communicate information about the near-field scene.

15. The optical-to-tactile translator of claim 14 wherein a variance in the intensity of the tactile shape signal is used to communicate depth of the near-field scene.

16. An optical-to-tactile translator for interpreting a near-field scene and communicating a tactile signal to a user based on said near-field scene comprising:
- an optical sensor to obtain said near-field scene and generate a visual interpretation signal corresponding to said near field scene and containing color information of said near-field scene;
- a tactile transmitter adapted to transmit a tactile shape signal containing color information to the user;
- a microprocessor in communication with said optical sensor for receiving said visual interpretation signal from said optical sensor, and based on said received visual interpretation signal, recognizing color information in said received visual interpretation signal, generating said tactile shape corresponding to said received visual interpretation signal, communicating said tactile shape signal to said tactile transmitter, and further commanding said tactile transmitter to transmit the tactile shape signal to the user.

17. The optical-to-tactile translator of claim 16 wherein said tactile shape signal conveys color information using vibrations of said tactile translator.

18. The optical-to-tactile translator of claim 1 including a plurality of tactile transmitters operating in conjunction with one another and separately located on the user.

19. The optical-to-tactile translator of claim 1 wherein said tactile transmitter comprises an array of pin members operably disposed adjacent a surface of said user for communicating said tactile shape signal, said communication achieved by a movement of selected pins defining said tactile shape signal until said pins contact said surface of said user.

20. The optical-to-tactile translator of claim 1 wherein said tactile transmitter comprises a single pin member movable over a surface of said user for communicating said tactile shape signal, said communication achieved by a series of repeated contacts and movements of said pin member where said series defines said tactile shape signal.

21. The optical-to-tactile translator of claim 1 wherein a sequence comprising the generation of said visual interpretation signal by said optical sensor, the generation and transmission of said shape signal by said microprocessor, and the delivery of the tactile shape signal by the tactile translator, is adjustable by the user.

22. The optical-to-tactile translator of claim 1 wherein a sequence comprising the generation of said visual interpretation signal by said optical sensor, the generation and transmission of said shape signal by said microprocessor, and the delivery of the tactile shape signal by the tactile translator, occurs more than once every second.

23. An optical-to-tactile translator for interpreting a near-filed scene and communicating a tactile signal to a user comprising:
- optical sensor means for obtaining said near-field scene and for generating a visual interpretation signal corresponding to said near-field scene;
- tactile transmitting means for transmitting a tactile shape signal in the form of a series of contacts by said tactile transmitting means with said user, said tactile shape signal corresponding to said near-filed scene; and
- microprocessing means operably connected to said tactile transmitting means and said optical sensor means for receiving said visual interpretation signal, performing gray-scale development and edge enhancement on said received visual interpretation signal, generating a shape signal corresponding to said edge enhanced visual interpretation signal, and communicating said shape signal and commands to implement said shape signal tactile transmitting means.

24. The optical-to-tactile translator of claim 23 further comprising range determining means cooperating with said optical sensor means for limiting the distance defining the near-field scene.

25. The optical-to-tactile translator of claim 23 further comprising means for recognizing common obstacles within said near-field scene, and for selecting a predetermined shape signal corresponding to said recognized common obstacle.

26. The optical-to-tactile translator of claim 23 wherein said optical sensor means comprises a plurality of active pixel sensors (APS).

27. The optical-to-tactile translator of claim 23 further comprising audible means for creating an audible signal to said user in conjunction with said tactile signal, said audible signal corresponding to said near-field scene.

28. The optical-to-tactile translator of claim 23 further comprising means for interpreting colors within said near-field scene, and means for communication said color interpretation in said tactile shape signal.

29. A method for translating a near-field visual representation to a tactile representation comprising the steps of:
- using an optical sensor having active pixel sensor technology to generate a digital signal corresponding to said near-field visual representation;
- communicating said digital signal to a microprocessor for processing said digital signal;
- performing gray-scale development and edge enhancement on said near-field representation;
- generating a shape signal corresponding to said edge enhanced near-field visual representation;
- communicating said shape signal to a tactile transmitter along with commands for delivering said shape signal; and
- delivering said shape signal in the form of contacts by said tactile transmitter defining said shape signal.

30. An optical-to-tactile translator for interpreting a near-field scene and communicating a tactile signal to a user based on said near-field scene comprising:
- an optical sensor to obtain said near-field scene and generate a signal corresponding to said near-field scene;

a range-determining device cooperating with said optical sensor to limit the distance that the optical sensor obtains the near-field scene;

a processor connected to said optical sensor to generate a tactile shape signal corresponding to said signal generated by said optical sensor; and a tactile transmitter connected to said processor to transmit the tactile shape signal to the user.

31. An optical-to-tactile translator for interpreting a near-field scene and communicating a tactile signal to a user based on said near-field scene comprising:

an optical sensor to obtain said near-field scene and generate a signal corresponding to said near-field scene;

a processor connected to said optical sensor to generate a tactile shape signal corresponding to said signal generated by said optical sensor, and to communicate the depth of said near-field scene in the tactile signal by varying the intensity of the tactile signal; and a tactile transmitter connected to said processor to transmit the tactile shape signal to the user.

32. An optical-to-tactile translator for interpreting a near-field scene and communicating a tactile signal to a user based on said near-field scene comprising:

an optical sensor to obtain said near-field scene and generate a signal corresponding to said near-field scene;

a processor connected to said optical sensor to generate a tactile shape signal corresponding to said signal generated by said optical sensor;

a tactile transmitter connected to said processor to transmit the tactile shape signal to the user, and configured to be removably mounted on the user's forehead.

33. The optical-to-tactile translator of claim 33 further comprising a housing member to house the optical sensor and tactile transmitter, and configured to be removably mounted on the user's forehead.

34. The optical-to-tactile translator of claim 34 further comprising a head band to secure the housing member to the user's forehead.

* * * * *